US006399086B1

(12) United States Patent
Katzhendler et al.

(10) Patent No.: US 6,399,086 B1
(45) Date of Patent: Jun. 4, 2002

(54) PHARMACEUTICAL PREPARATIONS FOR THE CONTROLLED RELEASE OF BETA-LACTAM ANTIBIOTICS

(75) Inventors: Ifat Katzhendler; Amnon Hoffman; Michael Friedman, all of Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/313,101

(22) Filed: May 17, 1999

Related U.S. Application Data

(63) Continuation of application No. PCT/IL97/00368, filed on Nov. 13, 1997.

(51) Int. Cl.[7] .......................... A01N 25/00; A61K 9/48; A61K 9/46; A61K 24/28; A61K 9/14

(52) U.S. Cl. .................. 424/405; 424/463; 424/466; 424/472; 424/474; 424/482; 424/484; 424/485; 424/486; 424/487; 424/488

(58) Field of Search ................. 424/405, 484, 424/486, 487, 488, 482, 485, 472, 466, 463, 474

(56) References Cited

U.S. PATENT DOCUMENTS

| 4,252,786 | A |   | 2/1981 | Weiss et al. .................. 424/19 |
| 4,462,934 | A | * | 7/1984 | Jasys ........................ 260/239 |
| 4,968,508 | A |   | 11/1990 | Oren et al. ................. 424/468 |
| 5,466,685 | A | * | 11/1995 | Brown-Skrobot et al. .. 514/199 |
| 5,545,485 | A | * | 8/1996 | Hashitani et al. ......... 428/423.1 |
| 5,626,874 | A | * | 5/1997 | Conte et al. ................ 424/464 |

FOREIGN PATENT DOCUMENTS

| EP | 0168044 | 1/1986 |
| GB | 1391554 | 4/1975 |
| GB | 1568837 | 6/1980 |
| WO | WO 9400112 | 1/1994 |
| WO | WO 9406416 | 3/1994 |
| WO | WO 9427557 | 12/1994 |
| WO | WO 9520946 | 8/1995 |
| WO | WO 9616638 | 6/1996 |

OTHER PUBLICATIONS

Rowland, M. and Tozer, T.N., *Clinical Pharmacokinetics* (2nd Edition 1989), pp. 23–24 (Exhibit 1).
"In Vitro an In Vivo Evaluation of an Oral Sustained–release Floating Dosage Form of Amoxycillim Trihydrate" Hilton et al.; Intrnational Journal of Pharmaceutics, 86 (1992).*

(List continued on next page.)

*Primary Examiner*—Thurman K. Page
*Assistant Examiner*—S. Tran
(74) *Attorney, Agent, or Firm*—John P. White; Cooper & Dunham LLP

(57) ABSTRACT

The present invention relates to a pharmaceutical controlled-release oral drug delivery system comprising as active ingredient at least one β-lactam antibiotic agent, having a specific absorption site in the small intestine in combination with a polymeric matrix, optionally further containing additional pharmaceutically acceptable constituents, wherein at least 50% of the β-lactam antibiotic agent are released from the matrix within from about 3 to about 4 hours from oral administration and the reminder of the pharmaceutical agent is released at a controlled rate. The drug delivery system according to the invention optionally further comprises a β-lactamase inhibitor, preferably in combination with amoxicillin and/or amoxicillin trihydrate as the active ingredient. The polymeric matrix of the pharmaceutical controlled-release oral drug delivery system of the invention my be of hydrophilic and/or hydrophobic nature and the delivery system may further comprise pharmaceutically acceptable additive. The pharmaceutical controlled-release oral drug delivery system of the invention is preferably in dosage unit form.

21 Claims, 3 Drawing Sheets

OTHER PUBLICATIONS

Arancibia, A. et al. (1987) "Pharmacokinetics and Bioavailability of a Controlled Release Amoxicillin Formulation" *Int. J. Clin. Pharmacol. Ther. Toxicol.* 25(2):97–100 (Exhibit 2),.

Evans, W.E. et al., *Applied Pharmacokinetics* (3$^{rd}$ Edition 1992), pp. 19–21 to –14 (Exhibit 3),.

Gibaldi, M., *Biopharmaceutics and Clinical Pharmacokinetics* (4$^{th}$ Edition 1991), pp. 24–27 (Exhibit 4),.

Guyton, A.C., *Textbook of Medical Physiology* (1971), pp. 765–774 (Exhibit 5);.

Hepner, G.W. et al. (1968) "Absorption Of Crystalline Folic Acid In Man" *Lancet* 2:302–306 (Exhibit 6);.

Hilton, A.K. et al. (1992) "In Vitro and In Vivo Evaluation of an Oral Sustained–release Floating Dosage Form of Amoxycillin Trihydrate" *Int. J. Pharm.* 86(1):79–88 (Exhibit 7);.

Hilton A.K. et al. (1993) "Use of Hydroxypropyl Methylcellulose Acetate Succinate in an Enteric Polymer Matrix To Design Controlled–Release Tablets of Amoxicillin Trihydrate" *J. Pharm. Sci.* 82(7):737–743 (Exhibit 8),.

Kalant, H. & Roschlau, W.H.E., *Principles of Medical Pharmacology* (5$^{th}$ Edition 1989), p. 549 (Exhibit 9);.

Levy, G. et al. (1966) "Factors Affecting the Absorption of Riboflavin in Man" *J. Pharm. Sci.* 55(3):285–289 (Exhibit 10);.

Matthews, D.M. (1983) "Intestinal Absorption of Peptides" *Biochem. Soc. Trans.* 11:808–810 (Exhibit 11),.

Mayersohn, M. (1972) "Ascorbic Acid Absorption In Man –Pharmacokinetic Implications" *Eur. J. Pharmacol.* 19:140–142 (Exhibit 12);.

Silk, D.B.A., et al. (1982) "Characterization and Nutritional Significance of Peptide Transport in Man[1]" *Ann. Nutr. Metab.* 26:337–352 (Exhibit 13); and.

Uchida, T. et al. (1989) "Biopharmaceutical Evaluation of Sustained–Release Ethycellulose Microcapsules Containing Amoxicillin Using Beagle Dogs" *Chem. Pharm. Bull.* 37(12):3416–3419 (Exhibit 14).

Hoffman A. et al. (1998) "Pharmacodynamic And Pharmacolkinetic Rationales For The Development Of An Oral Controlled–Release Amoxicillin Dosage Form" *Journal of controlled Release* 54 (1) :29–37 (Exhibit 11).

* cited by examiner

PHARMACEUTICAL PREPARATIONS FOR THE CONTROLLED RELEASE OF BETA-LACTAM ANTIBIOTICS

This application is a continuation of PCT International Application No. PCT/IL97/00368, filed Nov. 13, 1997 claiming priority of Israeli Patent Application No. 119627, filed Nov. 17, 1996, the contents of which are hereby incorporatedin their entireties into the present application.

FIELD OF THE INVENTION

The invention relates to controlled-release oral drug delivery system comprising as active ingredient at least one β-lactam antibiotic agent, particularly intended for the delivery of drugs having a specific absorption site.

BACKGROUND OF THE INVENTION

The selection of the appropriate mode of drug administration is of major importance since the efficacy of the drug greatly depends thereon. The selection should be based upon the pharmacokinetic and pharmacodynamic properties of the drug. While emphasis should be given to pharmacokinetic parameters, such as absorption characteristics, protein binding and clearance, less concern is given to the pharmacodynamic profile of the drug, i.e. the concentration-effect relationship. In the case of antimicrobial agents, this relationship depends on three elements: the pathogen, the host and the specific antimicrobial agent. The impact of the host, apart from the pharmacokinetic properties, depends mainly on its immune system. The relationship between drug concentration and its inhibitory effect on microbial growth for a certain drug-pathogen combination can be determined in vitro. While in certain cases (e.g. aminoglycosides) elevation of drug concentration is associated with enhanced bacteriocidal potency, other cases (such as β-lactam antibiotics and erythromycin) are not highly concentration-dependent. The post-antibiotic effect (PAE) of the drug is another pharmacodynamic parameter that has to be taken account of for the determination of an optimal dosage regime. The extrapolation of the in vitro data to an in vivo situation is less complex when the pathogen is located extracellularly, as in the case of β-lactam susceptible microorganisms.

In assessing the properties of β-lactam antibiotics in light of the principles outlined above, it has been concluded that an oral controlled-release preparation that would maintain low but effective concentrations for a prolonged period would be the suitable mode of administration of these medications. This conclusion is based on the following points: (1) The biological half-life of these agents is considerably short (about 1–2 hrs), which necessitates frequent administration; (2) Elevation of the drug concentration above a critical value which tends to be the minimal inhibitory concentration (MIC) is not associated with increased bacteriocidal potency; (3) There is a direct correlation between the time above MIC and o antimicrobial potency. There is no correlation between Area Under Curve (AUC) values and the drug's efficacy; (4) It has been confirmed that continuous infusion is advantageous to periodic bolus administration of these agents; (5) For these drugs there is a minimal effective concentration before the bacteriocidal effect is noted; (6) With the single exception of penem antibiotics, all the β-lactams exhibit either no PAE or a very short PAE; (7) High concentrations are associated with reduced potency; (8) The penetration of the drug into the tissues is not correlated to the serum concentration, i.e., elevation of serum drug concentrations will not contribute much in cases where the pathogen is located intracellularly; (9) Unlike aminoglycosides, the kinetics of the bacteriocidal effect are slow and require maintenance of drug effective concentration for a certain lag time to the onset of effect.

Hilton and Deasy [J. Pharm. Sci. 82(7):737–743 (1993)] described a controlled-release tablet of amoxicillin trihydrate based on the enteric polymer hydroxy-propylmethyl cellulose acetate succinate. This polymer suppressed the release of the drug in the presence of gastric pH but could enhance its release in the small intestine. Therefore, such a formulation cannot give the desired burst effect discussed below. Single dose studies with a panel of fasting subjects showed that the tablets had a relative bioavailability of only 64.4%, probably because the poorer absorption of amoxicillin from the distal jejunum and ileum than from the duodenum and proximal jejunum. Other pharmacokinetic parameters confirmed a lack of therapeutic advantage of these factors over an equivalent dose of conventional capsule.

Hilton and Deasy [Int. J. Pharm. 86(1):79–88 (1992)] also described a floating tablet of amoxicillin trihydrate. A bilayer tablet was initially formed in which the controlled-release drug layer consisted of amoxicillin and hydroxypropyl cellulose. This layer was bonded to a gas generating layer. However, when the two layers were joined together, the composite tablet failed to float and prematurely split along the joining of the two layers. Consequently, it was decided to abandon this approach in favor of a single-layer floating tablet. This tablet remained buoyant for 6 hours and had satisfactory in vitro sustained release. However, compared with conventional capsules in fasting humans at 500 mg equivalent dose of amoxicillin, the relative bioavailability of the tablets was 80.5% and other pharmacokinetic parameters $T(0.1 \mu g/ml)$ and $T(0.5 \mu g/ml)$ corresponding to the length of time for which the serum levels remained greater than or equal to 0.1 $\mu g/ml$ and 0.5 $\mu g/ml$, respectively, indicated lack of improved efficacy.

Uchida et al. [Chem. Pharm. Bull. 37(12):3416–3419 (1989)] described a preparation of amoxicillin microencapsulated in ethyl cellulose. These micro-capsules exhibited a sustained-release effect when administered to dogs. However, such effect could be foreseen, since the gastric pH of the dogs which were tested is considerably higher than human gastric pH (pH of about 6 in beagle dogs, compared to pH of about 2 in humans).

The amoxicillin is much less soluble at pH=6 than at pH=2. One would expect to obtain a very quick release of the drug from the same microcapsules if administered to humans. Such fast release would be identical to release from the pure drug, and not controlled.

Arancibia et al. [Int. J. Clin. Pharmacol. Ther. Toxicol. 25(2):97–100 (1987)] investigated the pharmacokinetics and bioavailability of amoxicillin trihydrate. They refer to controlled-release tablets, the composition of which is not described. In any case, no drug was detectable after 8 hours from oral administration and therefore this formulation had no advantage over conventional formulations.

The aim of this invention is therefore to provide oral controlled-release preparations of various drugs, preferably of β-lactam antibiotics, and particularly the widely used amoxicillin, in order to optimize pharmacotherapy with these drugs. An important approach for such optimization is to improve patient compliance by minimizing the frequency of drug administration to once or twice a day.

SUMMARY OF THE INVENTION

The invention relates to a pharmaceutical controlled-release oral drug delivery system comprising as active ingredient at least one β-lactam antibiotic agent having a specific absorption site in the small intestine in combination with a polymeric matrix, optionally further comprising additional pharmaceutically acceptable constituents, wherein at least 50% of said β-lactam antibiotic agent are released from said matrix within from about 3 to about 4 hours from oral administration and the remainder of said pharmaceutical agent is released at a controlled rate.

The drug delivery system of the invention may further comprise a β-lactamase inhibitor.

The polymeric matrix may comprise a hydrophilic polymer, a hydrophobic polymer or mixtures thereof.

The drug delivery system of the invention may be in any suitable dosage unit form.

DETAILED DESCRIPTION OF THE INVENTION

Figure 1:
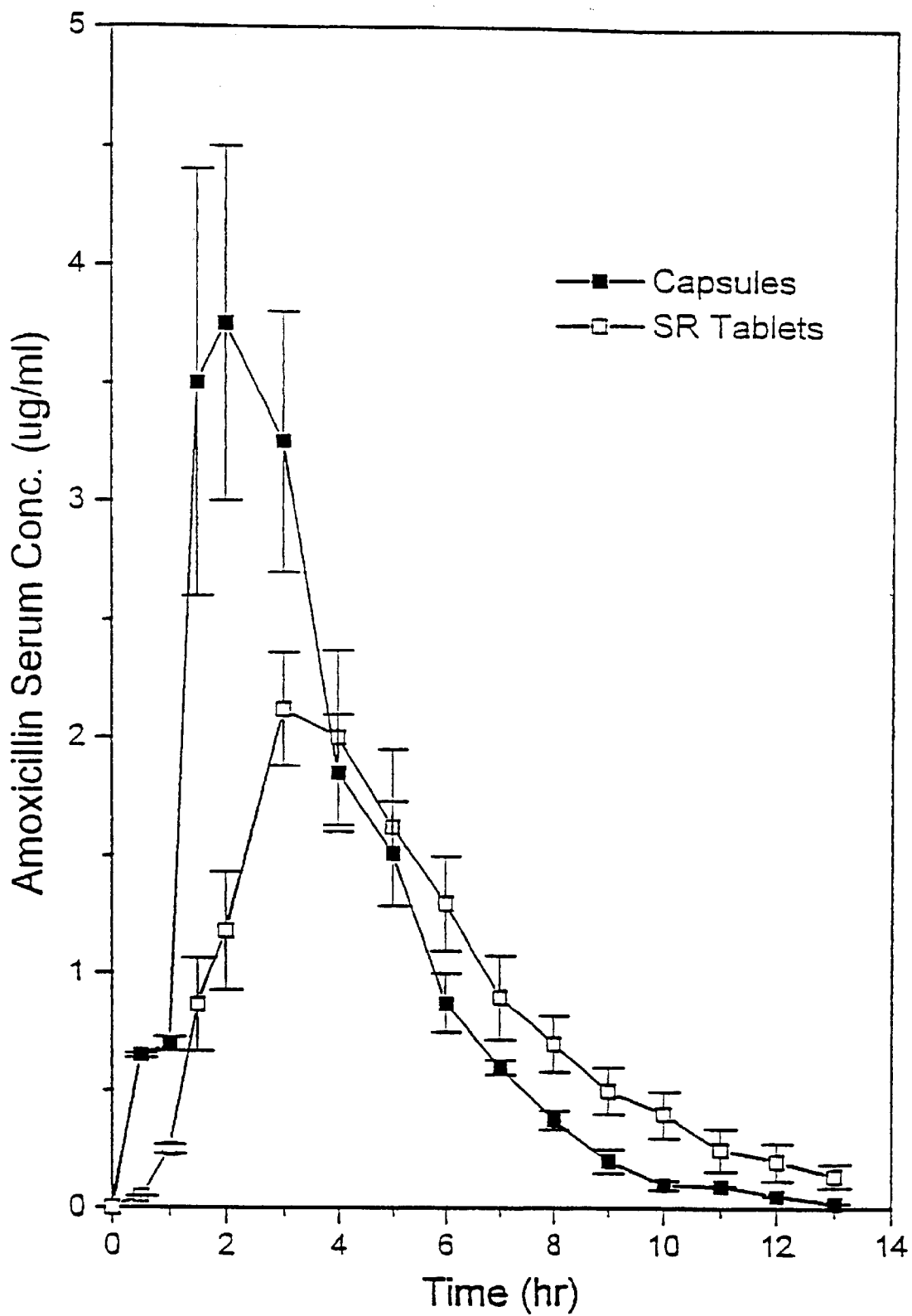
FIG. 1 Mean serum amoxicillin concentration vs. time profile in 12 subjects of formulation A3 (-□-□-) in comparison with 500 mg amoxicillin capsules (MoxyvitR), (-■-■-) Bar: 1±SE. (Example 4).

The present invention relates to a pharmaceutical controlled-release oral drug delivery system comprising as active ingredient at least one β-lactam antibiotic agent having a specific absorption site in the small intestine in combination with a polymeric matrix, optionally further containing additional pharmaceutically acceptable constituents, wherein at least 50% of said β-lactam antibiotic agent are released from said matrix within from about 3 to about 4 hours from oral administration and the remainder of said pharmaceutical agent is released at a controlled rate.

The drug delivery system of the invention may be effective with any pharmaceutical agent which has an "absorption window". The term "drugs which have an absorption window" as currently used in the art refers to drugs which are absorbed at specific sites in the gastrointestinal tract, for example drugs which are absorbed by carrier-mediated mechanisms. Such mode of absorption is suggested for compounds like dipeptides [Matthews, D. M., Biochem. Soc. Trans. 11:808–810 (1983)], riboflavin [Levy, J. & W. Jusko, J., J. Pharm. Sci. 55:285–289 (1966)], folic acid [Hepner, G. W. et al., Lancet 2:302–306 (1968)] and ascorbic acid [Mayersohn M., Eur. J. Pharmacol. 19:140–142 (1972)]. Penicillin may be regarded as a dipeptide derived from cysteine and valine [Doyle, F. P. & Nayler, J. H. C., Advances in Drug Research 1:8–13, (1964); Harper, N.J. & Simmonds, A.B. Eds. Academic Press] and is thus absorbed by a special transport mechanism common to the absorption mechanism of dipeptides, for which a suitable transport system has been demonstrated in man [Matthews, D. M., ibid.; Silk, D. B. A. et al., Ann. Nutr. Metab. 26:337–352 (1982)].

Another mechanism for drugs which are absorbed at a specific absorption site is associated with drugs which are solubilized at a specific locus in the gastrointestinal tract, for examples fats. A specific illustrative example for this mechanism is tocopherol which is solubilized by bile acid micelles [Guyton, A. C., Textbook of Medical Physiology, W.B. Saunders Company, (1986)]. Further examples of drugs which are absorbed by carriers are salts [Guyton, A. C., (1986) ibid.] AZT, 5-FU, α-methyl-Dopa and L-Dopa, riboflavin [Gibaldi, M., Biopharmaceutics and Clinical Pharmacokinetics, 3rd Edition, (1984); Evans, W.E. et al., Applied Pharmacokinetics 19:1–14 (1992); Rowland, M. & Tozer, T.N., Clinical Pharmacokinetics, concepts and applications, pp 23–24, (1988), Lea & Febiger, Philadelphia].

According to the preferred embodiments of the present invention, the β-lactam antibiotic drug capable of providing the desired burst effect, is cephalosporin and/or a penicillin. Examples of cephalosporins which may be used with the delivery system of the invention are cefadroxil, cefalexin, cefaclor, cefprozil, cefuroxime, cefoxitin, cefpodoxime, cefixime, pharmaceutically acceptable salts thereof or pharmaceutically acceptable derivatives thereof. Examples of penicillins which may be used in the delivery system of the invention are penicillin G, penicillin V, amoxicillin, ampicillin, nafcillin, oxacillin, cloxacillin, dicloxacillin, or pharmaceutically acceptable salts thereof. Examples for pharmaceutically acceptable cephalosporin derivatives, which may be used in the delivery system of the invention, are cefpodoxime proxetil and cefuroxime axetil.

In a particularly preferred embodiment of the present invention the drug delivery system of the invention contains as the β-lactam agent amoxicillin trihydrate or pharmaceutically acceptable salts thereof. A mixture of the active antibiotic agent with a pharmaceutically acceptable salt thereof can also be used as the active pharmaceutical agent in the delivery system of the invention. Thus, for example, it may be advantageous to use a mixture of amoxicillin with amoxicillin sodium salt in order to provide the desired burst effect.

It may be advantageous to add to the drug delivery systems of the invention a β-lactamase inhibitor. Suitable β-lactamase inhibitors are clavulonic acid or sulbactam. β-lactamase inhibitors themselves have poor antibacterial activity. However, when given in combination with penicillins, to treat infections involving β-lactamase producing bacteria, they enhance the antibiotic effect [Kalant, H. & Roschlau, W. A. E., Principles of Medical Pharmacology, 5th Ed., pp 549 (1989) B. C. Decker Inc.].

The drug delivery system of the invention may further optionally contain additional pharmaceutical agents having a specific absorption site in the small intestine, for example, vitamins such as riboflavin, folic acid, ascorbic acid, thiamin or tocopherol or mixtures thereof, anti-viral agents such as AZT, antitumor agents, therapeutic metal inorganic salts such as iron salt, lithium salt or potassium salt, antihypertensive agents such as α-methyl Dopa and antiparkinsonian agents such as L-Dopa. The drug delivery system of the invention may also fiber contain a mixture of such agents, e.g. a mixture of vitamin/s with other therapeutic agents, for example metals. A specific example may be a mixture of iron and folic acid.

In a first aspect, within the drug delivery system of the invention, the polymeric matrix comprises a hydrophilic polymer. Examples of hydrophilic polymers which may be suitable as the matrix of the delivery system of the invention are hydrophilic cellulose derivatives, hydrophilic polyacrylamide derivatives, proteins, alginates, arabino-galactane, chitosan and hydrophilic methacrylic acid derivatives. Preferred hydrophilic cellulose derivatives are methyl cellulose, hydroxypropyl methylcellulose, hydroxyethyl cellulose, hydroxypropyl cellulose, carboxymethyl cellulose, sodium carboxymethyl cellulose and hydroxyethylmethyl cellulose. Most preferred is hydroxypropylmethyl cellulose (HPMC). HPMC is particularly preferred for use with amoxicillin. Since amoxicillin has a very low solubility, the use of matrices comprising low viscosity erodible polymers is desired. The rate of release of amoxicillin from the tablets is controlled by the erosion mechanism. The tablet is eroded by zero-order kinetics. Since the tablet surfaces are decreases with time, amoxicillin release rate will be higher at earlier stages of dissolution.

Specific HPMC's which are suitable are Methocel$^R$ K100M, K15M, K4M, K100LV, K3, F4M, E4M, E50LV, E10M, E6, E5 and E3 and any other HPMC of pharmaceutically acceptable grade.

When using Methocel K100LV, the ratio of drug:polymer is preferably from about 4:1 to 10:1. If a release accelerating agent is added, higher concentrations of polymer can be used. For Methocel K4M, K15M or K100M, lower concentrations of about 10% polymer or less are desired.

Since at lower concentrations of polymer the tablet may disintegrate due to the formation of incomplete gelatinous layer, it is preferable to incorporate a release accelerating agent in the system. For example, in a formulation containing 20% polymeric carrier such as Methocel K4M and a release accelerating agent, the release accelerating agent preferably comprises at least 50% of the polymeric carrier.

For Methocels of lower viscosity grades, such as K3, E50LV, E15LV, E10M, E6, E5 and E3, a ratio higher than 4:1 (drug:polymer) can be used, due to their higher erosion rate.

In general, the ratio of drug:polymer will be varied according to the size and shape of the tablets, since the rate of release of the drug depends also on the ratio of the tablet's surface are to its volume. The above examples refer to tablets of 12 mm diameter containing 500 mg amoxicillin trihydrate.

In cases where the active pharmaceutical agent is a mixture of an antibiotic drug and its salt, higher concentrations of polymer, such as HPMC, or lower concentrations of the release accelerating agent may be employed.

Protein which are suitable as the polymeric carriers are, for example, egg, albumin, bovine albumin, human albumin or soy bean protein. The proteins can be used in the native or denatured form. Denatured proteins can be prepared by any acceptable method, as known to the man skilled in the art.

The polymeric matrix of the drug delivery of the invention may also comprise a hydrophobic polymer. Suitable hydrophobic polymers are hydrophobic cellulose derivatives, such as ethyl cellulose, fats, such as glycerol palmitostearate, beeswax, glycowax, castorwax, carnaubawax, glycerol monostearate or stearyl alcohol, hydrophobic polyacrylamide derivatives and hydrophobic methacrylic acid derivatives.

In order to provide the desired burst effect with hydrophobic polymeric matrices, it would be preferable to add to the delivery system of the invention release accelerating agents, preferably at high concentrations.

Example of suitable release accelerating agents are polyethylene glycol and salts, but other pharmaceutically acceptable accelerating agents may be suitable, as known to the man versed in the art of pharmacy.

Alternatively, granules comprising the antibiotic agent and polymer may be prepared and mixed with a powder of the antibiotic agent and compressed into tablets. The free drug would provide the burst effect, while the granules would release the drug contained therein at a controlled rate.

Still alternatively, double-layer tablets may be prepared in which one layer would contain the free drug, providing the burst effect, and the second layer would contain the drug in combination with the polymer, providing for controlled release of the active drug.

The polymeric matrix may comprise a mixture of any of said hydrophilic polymers, a mixture of any of said hydrophobic polymers or a mixture of such hydrophilic and hydrophobic polymers.

The drug delivery system of the invention may further comprise a pharmaceutically acceptable additive selected from salts, polyethyleneglycol and surfactants.

The present invention drug delivery system may also contain a pharmaceutically acceptable binder. Pharmaceutically acceptable binders suitable for use in the present invention are chosen from those routinely used by formulation chemists and include sucrose gelatin, acacia, tragacanth, cellulose derivatives, povidone, polyethylene glycols and other binders known to those familiar with pharmaceutical formulations.

If desired, other conventional tablet ingredients such as lubricants, stabilizers and glidents may be included in the present drug delivery system.

The formulations may be prepared by procedures well known to formulation chemists.

The drug delivery system of the invention can be in dosage unit form. Specific examples of the delivery system of the invention are mono-or double-layer tablets, tablets which disintegrate into granules, capsules, or any other means which allow for oral administration. These forms may optionally be coated with a pharmaceutically acceptable coating. Such coating may comprise a biodegradable polymer, a coloring and/or flavoring agent or any other suitable coating. The techniques of preparing coated formulations are known to the man versed in the art of pharmacy.

The amount of the active pharmaceutical agent can vary as desired for efficient delivery of the desired agent, and in consideration of the patient's age, weight, sex, disease and any other medical criteria and will be determined according to techniques known in the art. The pharmaceutical dosage forms of the invention may be administered once or more times a day, as will be determined by the attending physician.

The invention is illustrated in more detail in the following Examples. While the examples specifically present the use of the delivery system of the invention with amoxicillin as the active pharmaceutical agent, the delivery system of the invention can be employed for any drug which has an "absorption window". As may be seen in FIG. 1 both $C_{max}$ and AUC were significantly higher from the prior art capsules. The differences in the pharmacokinetic parameters which seem to indicate poor bioavailability have no relevance from the therapeutic point of view. The important factor is the time period over the MIC. High $C_{max}$ values do not correspond to increased efficacy.

Figure 2:
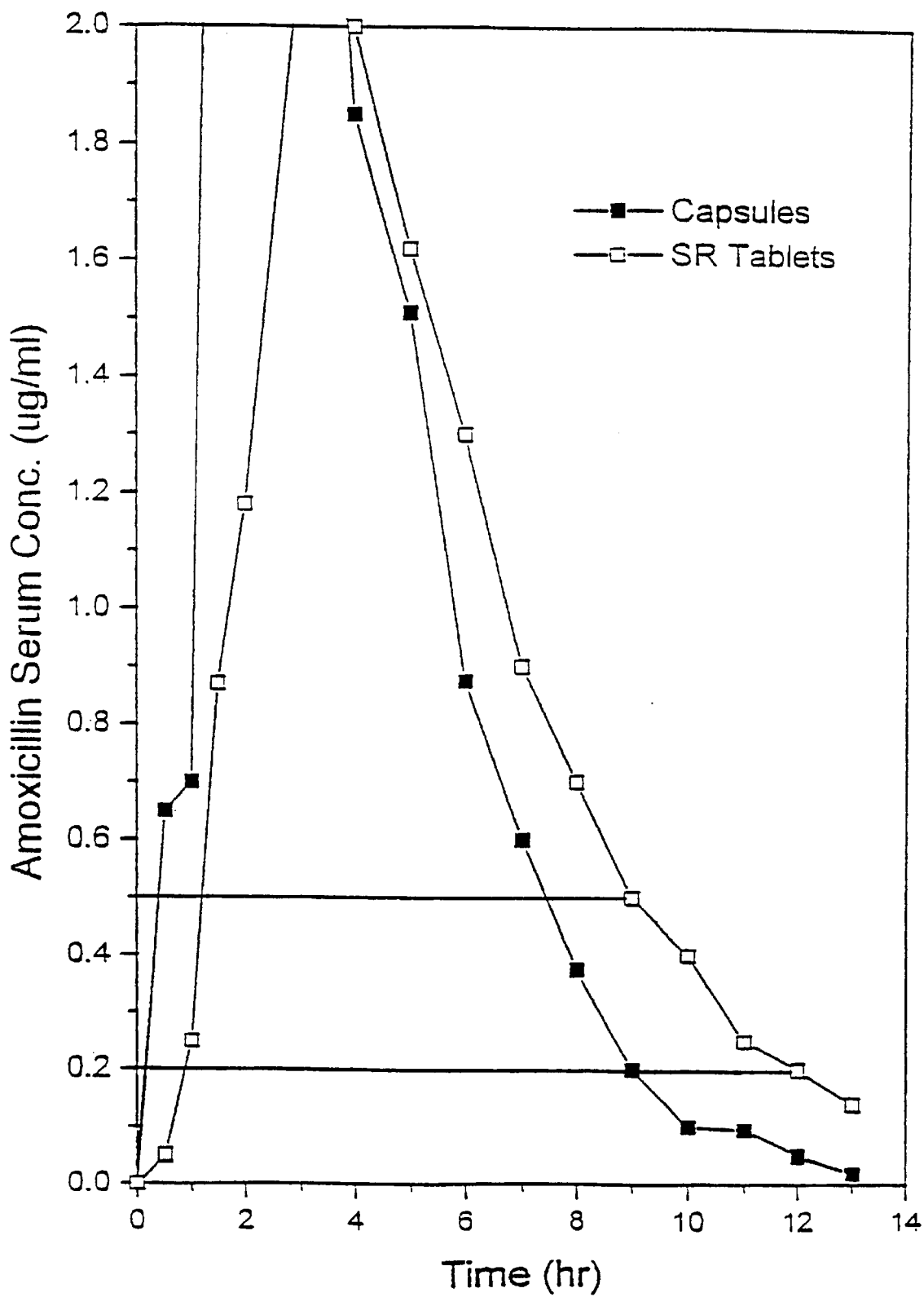
FIG. 2 The lower portion of FIG. 1 (amoxicillin concentration up to 2 mg/L) at a larger scale.

The selection of the appropriate antibiotic is based on the susceptibility of the pathogen. There would be no sense in using amoxicillin for pathogens that are not sensitive thereto and have MIC values higher than 1 mg/L. In fact, the amoxicillin MIC for most of the microorganisms against which it is prescribed are not higher than 0.5 mg/L. Specifically, Streptococci group A, 0.01 mg/L; *Streptococci pneumoniae*, 0.02 mg/L; *Staphylococcus aureus*, 0.1 mg/L;

*Haemophilus influenza* 0.25 mg/L; *Enterococcus faecalis*, 0.5 mg/L. Therefore, unlike the common pharmacokinetic analysis of the concentration vs. time profile, the pharmacodynamic profile of the drug indicates that the comparison between the two formulations should concentrate on the time over the MIC. As shown in FIG. 2, the sustained release formulation provides 1.5 hrs greater coverage than the capsules for MIC=0.5 mg/L and about 3 hrs longer for MIC=0.2 mg/L.

In principle, extending the residence time of the antibiotic drug in the GI tract by s the sustained release formulation may increase, in theory, the GI adverse effects associated with amoxicillin therapy. Obviously, such phenomenon of increased risk of side effects is a limitation for the development of amoxicillin controlled-release formulations. However, in the formulations of the present invention, the unabsorbed portion of the dose that had a prolonged transit time in the GI tract is captured within the matrix formulation and is not available to interact with the intestine epithelia and/or flora, thus eliminating the danger of exposing the patient treated with the formulations of the present invention to said adverse side effects.

Figure 3:
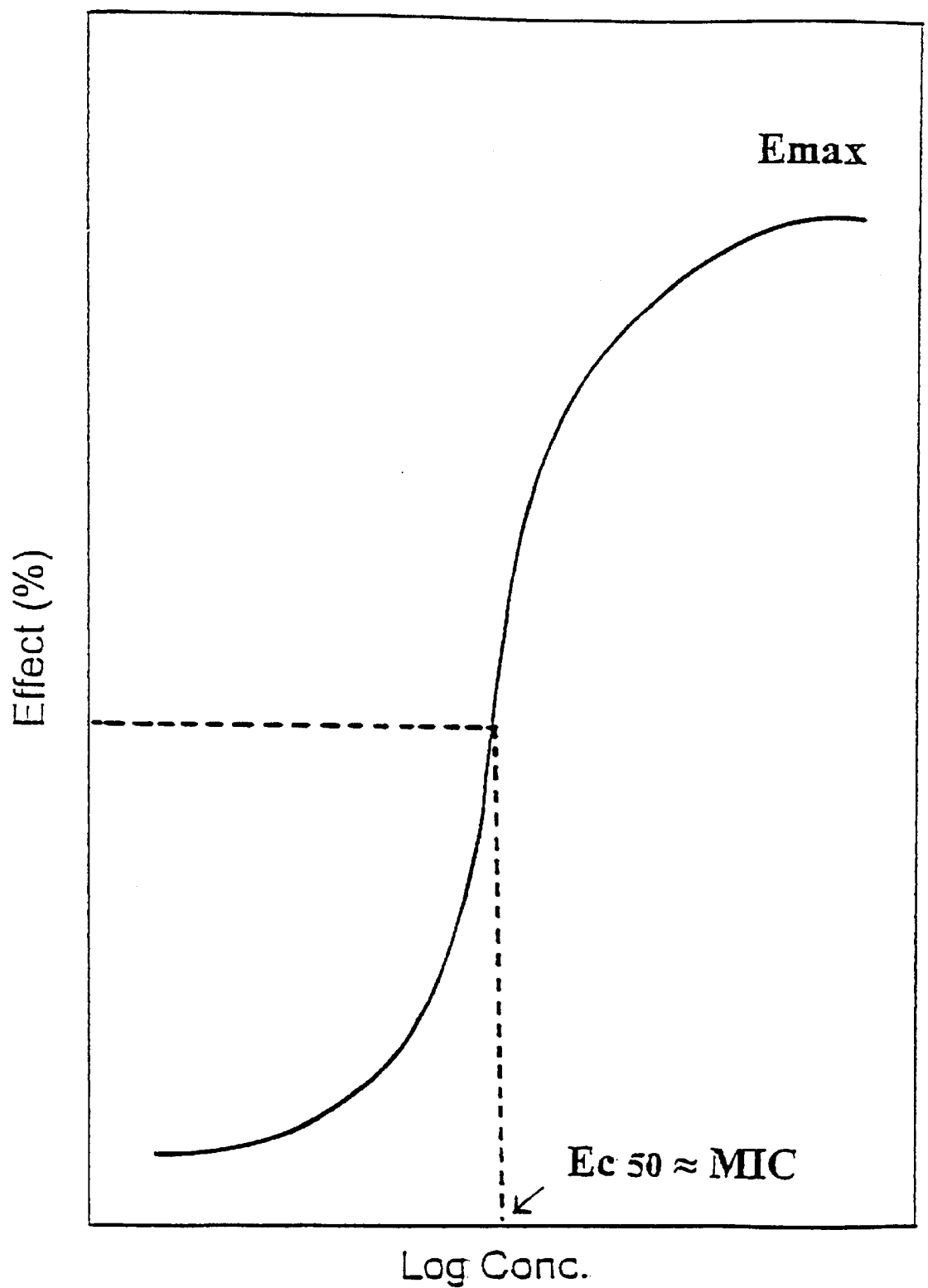
FIG. 3 Simulation of the effect vs. concentration according to the sigmoidal $E_{max}$ model with shape parameter n=71.5, describing the pharmaco-kinetic profile of amoxicillin.

The pharmacodynamic profile of amoxicillin can be described by the sigmoidal $E_{max}$ model with a shape parameter larger than 1.5 (characterized by a steep profile) as described in FIG. 3, where the MIC is the $EC_{50}$ value. This presentation clearly explains the situation where the drug concentrations that are significantly greater than the MIC are close to the maximal effect $E_{max}$ and contribute only little to the efficacy.

The invention will be described in more detail on hand of the following Examples, which are illustrative only and do not limit the scope of the invention, which is defined by the appended claims.

EXAMPLES

Example 1

(I) Matrix Tablets Containing Hydroxypropylmethyl Cellulose

Methods

Assay of Active Agent

Amoxicillin concentration was determined spectrophotometrically at 272 nm. Concentrations were determined from a suitable calibration curve.

Determination of Stability of active Agent in the Dissolution Medium

Solution with known concentrations of amoxicillin were prepared according to USP XXI (P.1420): phosphate buffer pH=6.8, 7.4, aceitc buffer pH=1.2, 2.0 and stored at 37° C.

Following 1, 2, 4, 6, 8 and 24 hrs the absorption profile of the drug between 200 nm and 300 nm was determined and compared with the absorption profile of the solutions before storage.

Determination of Solubility of Active Agents in Solvents of the Dissolution Medium Tests at 37° C.

Super-saturated solutions of the active agents were shaken at 37° C. for 24 hrs in different solvents. Due to instability of amoxicillin solutions at pH=2, the solutions were shaken only for 6 hrs. Solubility at pH=1.2 was not determined due to lack of stability.

The solutions were filtered. Concentration of the active agent was determined in each filtrate after suitable dilution at 37° C.

Methods of Preparing Matrix Tablets

Various mixtures of amoxicillin and hydroxypropyl methylcellulose were mixed geometrically and manually compressed under 5 tons pressure for 30 sec. The surfaces of the tablet were concave. Content of active agent: 500 mg amoxicillin trihydrate. Diameter: 12 mm.

Dissolution Rate Test (DRT) of Amoxicillin from Tablets

A. Instruments—DRT was performed in Tablet Dissolution Tester Model 7 ST. Caleva, USA.

B. Matrix tablets were placed in standard baskets. Rate of dissolution was determined using the tester at 100rpm and 37° C.

Extraction solvent was pH=7.4 buffer, unless otherwise indicated. Volume of the extraction solvent was 250–900 ml and enabled preserving sink conditions all along the release (volume of solvent was changed according to the formulation in order to increase the sensitivity of the analytical method).

Aliquots, 5 ml each, were taken from the extracts every 0.5, 1, 2, 3, 4, 5 and 6 hours and content of active agent was determined spectrophotometrically as described. Experiments were conducted in triplicates (deviation from average $\leq \pm 5\%$).

Influence of Viscosity of Hydroxypropyl Methylcellulose on Release of the Active Agent Tablets containing 70% amoxicillin and 30% hydroxypropyl methylcellulose of different viscosities were prepared: Methocel K100LV (100 cps), Methocel K4M (4,000 cps) and Methocel K15M (15,000 cps).

The tablets were placed in the dissolution tester and DRT was determined as above.

Influence of Concentration of Hydroxypropyl methylcellulose on Rate of Release from the Matrix Tablets Tablets containing different concentrations (10%, 15%, 20%, 30% and 50%) of Methocel K100LV and Methocel K4M were prepared.

Tablets were placed in the dissolution tester and DRT was determined as above.

Influence of the Type and Concentration on the Release Accelerating Agent of the Rate of Release from the Matrix Tablets Release accelerating agent: PEG 4,000; PEG 1,500; PEG 400; NaCl; and NaHCO$_3$.

These release enhancing agents were added to mixtures containing the active agent and Methocel K4M at 5% 10% w/w of the total tablet weight (the amount of the release agent added was on account of the polymer content). The tablets were of constant weight for the different formulations (625 mg). The polymer and the release accelerating agent constituted 20% of the weight of the tablet.

Tablets were placed in the dissolution tester and DRT was determined as above.

Influence of sodium Amoxicillin on Rate of Release

The following formulations were prepared:

| | | |
|---|---|---|
| 1. | Amoxicillin trihydrate | 400 mg |
| | Amoxicillin sodium | 92.6 mg |
| | Methocel K4M | 125 mg |
| 2. | Amoxicillin trihydrate | 300 mg |
| | Amoxicillin sodium | 125 mg |
| | Methocel K4M | 125 mg |
| 3. | Amoxicillin trihydrate | 462.5 mg |
| | Methocel K4M | 125 mg |

Sodium amoxicillin was ground before its addition to the powder mixtures.

Tablets were placed in the dissolution tester and DRT was determined as above.

For Formulation No. 2, in addition to the dissolution test at pH=7.4, the tablets were introduced to an acidic medium (pH=2) for 2 hrs, and then transferred to the pH=7.4 buffer.

Influence of Size on the Granulate of Release of Amoxicillin

Amoxicillin was granulated by PVP K-30 (5% in isopropanol): Granules were sieved in 30, 40 and 60 mesh sieves and dried at 37° C. Granules were mixed with Methocel K4M.

Tablets were placed in the dissolution tester and DRT was determined as above. In addition compacted amoxicillin was tested. Tablets containing 80% compacted amoxicillin and 20% Methocel K4M were prepared.

Influence of the pH of the Extraction Medium on Rate of Release from Matrix Tablets Tablets containing 20% Methocel K4M were introduced to a dissolution medium of pH=7.4, pH=6.8 and pH=2. DRT was performed as above.

Influence of Compression on Rate of Release from Matrix Tablets

Tablets containing 20% Methocel K4M were compressed under 1, 3, 5 and 8 tons.

Tablets were placed in the dissolution tester and DRT was determined as above.

Influence of RPM on Rate of Release

Tablets containing 20% Methocel K4M were placed in the dissolution tester and DRT was determined as above at 50, 100, and 200 rpm.

Rate of Release from Commercially Available Capsules

Commercial amoxicillin capsules (Moxypen Forte) were placed in the dissolution tester and DRT was determined as above. Aliquots, 5 ml each, were taken every 25, 0.50, 1.5, 2 and 4 hrs. The aliquot were filtered through sintered glass. Empty capsules were placed in the tester and aliquots were collected at same times. The aliquots from the capsules with active agent were read against aliquots from the empty capsules.

Characterization of the Release Kinetics of Amoxicillin from a Single Surface

Preparation of Tablets: 12 mm diameter tablets were prepared from mixtures of 500 mg amoxicillin and 20% Methocel K4M; 10% Methocel K4M; 10% PEG 4,000 and 10% Methocel K4M. The mixtures were compressed under 5 tons. Surfaces of the tablets were planar. The tablets were coated with paraffin wax, melted to 37° C. so that only one surface remained uncoated. Dissolution rate was determined using a paddle system.

Materials

Amoxicillin trihydrate powder, Teva, Israel
Amoxicillin trihydrate powder, Vitamed, Israel
Amoxicillin compacted, Vitamed, Israel
Amoxicillin sodium, Vitamed, Israel
Methocel K4M, Dow, USA
Methocel K100LV, Dow, USA
Methocel K15, Dow, USA
Potassium dihydrogen phosphate, Riedle-deHaen
Sodium hydroxide (pellets), analytical, Frutarom, Israel
Hydrochloric acid, Frutarom, Israel
PEG 400, Union Carbide, USA
PEG 1,500 (1.450 Flake NF), Union Carbide, USA
PEG 4,000 (4.600 Flake NF), Union Carbide, USA
Sodium chloride, Frutarom, Israel
Sodium bicarbonate, Merck, Germany
PVP K-30, MCA, USA
Isopropyl alcohol, Frutarom, Israel
  Drugs
  Moxypen Forte (500 mg), Teva, Israel
  Moxyvit (500 mg), Vitamed, Israel
  Instruments
  Tablet Dissolution Tester Model 7ST Caleva USA.
Uvicone 930 Kontron spectrophotometer, Switzerland
KBr disk device Results A. Solubility and Stability Amoxicillin was stable at pH=7.4 and pH=6.8 after 24 hrs and at pH=2 after 6 hrs. At pH=1.2 deterioration occurred after 1hr.

Solubilities were as follows:

| | |
|---|---|
| pH = 2 | 10.37 mg/ml |
| pH = 6.8 | 6.99 mg/ml |
| pH = 7.4 | 9.03 mg/ml |

The pH=7.4 buffer was selected as the extraction medium in all of the experiments for reasons of solubility and stability.

B. Influence of the Viscosity of HPMC on Release of the Active Agent

Lowering the viscosity of the polymer resulted in increased rate of release.

| Polymer | Amount released after 6 hours |
|---|---|
| 30% Methocel K100LV | 55.13% |
| 30% Methocel K4M | 20.19% |
| 30% Methocel K15M | 14.19% |

C. Influence of Concentration of HPMC on Release of Amoxicillin

Lowering the amount of polymer caused an increase in rate of release. For Methocel K4M, reducing the polymer content from 50% to 10% resulted in an increase of release of amoxicillin, after 6 hrs, from 17.7% to 58.8%. For Methocel K100LV, reducing the polymer content from 50% to 10% resulted in an increase of release of amoxicillin, after 6 hrs, from 35.1% to 100%.

D. Influence of the Type and Concentration of the Release Accelerating Agent on the Rate of Release The addition of the release accelerating agents PEG 4,000, PEG 1,500, PEG 400, NaCl and $NaHCO_3$ to the formulation caused an increase in the rate of release of the active agent compared to a formulation containing 80% amoxicillin and 20% Methocel K4M.

Release of amoxicillin from a formulation containing 10% release accelerating 1o agent was greater than from a formulation which contained 5% release accelerating agent. There was no significant difference between PEG 4,000, PEG 1,500 and PEG 400 in accelerating the release. NaCl caused a higher increase in release of amoxicillin compared to PEG 4,000, PEG 1,500 and PEG 400. The addition of 5% $NaHCO_{03}$ to the formulation caused a burst effect and a higher rate of release compared to the other accelerating agents added in identical concentrations. Tablets which contained 10% $NaHCO_3$ disintegrated.

E. Influence of Sodium Amoxicillin on Rate of Release

Increase in content of amoxicillin sodium in the formulation caused a higher burst effect and increase in release. Pre-treatment at pH=2 caused an insignificant reduction of the burst effect.

F. Influence of Size of the Granulate of Release of Amoxicillin

Increase in the size of the granulate increased the percentage of amoxicillin released, from 30.4% to 37.8% after 6 hrs, for granulates passed through 60 mesh and 30 mesh sieves, respectively. For the formulation which contained compacted amoxicillin, 40% were released after 6 hrs. Increase in the size of granule in formulations containing low concentration of the polymer reduced the strength of the gel layer and therefore increased the erosion rate.

G. Influence of the pH the Extraction Medium on Rate of Release

Release of amoxicillin was faster at pH=7.4 than at pH=6.8, but there was no significant difference. Release of amoxicillin at pH=2 was somewhat faster than at pH=7.4 and pH=6.8.

H. Influence of Compression on Rate of Release

Changing the compression pressure over a range of from 1 to 8 tons did not significantly change the rate of release.

I. Influence of RPM on Rate of Release

Increase in RPM increased the rate of release.

J. Rate of Release from Commercially Available Tablets

Dissolution from commercially available Moxypen Forte capsules was very fast, 83.2% dissolved after 15 min. and complete dissolution was observed after 30 min.

K. Characterization of the Release Kinetics of Amoxicillin from a Single Surface Release of amoxicillin from a single surface was of zero-order for the tested formulations. Release of amoxicillin from a formulation which contained 10% PEG 4,000 and 10% Methocel K4M was faster than from a formulation which contained 20% Methocel K4M.

Summary

This experiment was conducted with the aim of creating controlled release of amoxicillin by entrapping amoxicillin in a hydrophilic hydroxypropyl methylcellulose matrix. All of the formulations achieved this purpose.

The rate of release of amoxicillin from the matrix tablets can be controlled in several ways:

a. by employing HPMC of different viscosity rates, since lower viscosity causes higher release of the active agent;
b. by altering the concentration of HPMC, since the higher the concentration, the lower is the release of the active agent;
c. by increasing the concentration of release accelerating agents, which increases the rate of release. A similar effect can be achieved by reducing the content of HPMC;
d. by increasing the solubility of the active agent in the extracting medium (by changing the pH, adding NaHCO$_3$ or using sodium amoxicillin), which causes increase in release of the active agent; and
e. by increasing the rotation velocity, which caused faster release due to erosion of the tablet.

(II) Release of Amoxicillin from a Formulation Based on Methocel K100LV and Methocel K4M Materials and Methods Formulations:

A. Tablets based on Methocel K100LV containing 20% sodium amoxicillin. Sodium amoxicillin was added on account of amoxicillin trihydrate, while the active agent constituted 80% from the total mixture.

B. Formulation on basis of Methocel K100LV containing 80% amoxicillin trihydrate, without sodium amoxicillin.

C. Formulation containing sodium amoxicillin and amoxicillin trihydrate, the sodium amoxicillin constituted 30% of the active agent, total active agents 80% of the total content.

D. Formulation containing 80% amoxicillin trihydrate, the polymeric matrix comprising a mixture of 50% Methocel K4M and 50% Methocel K100LV.

| | | |
|---|---|---|
| A. | Amoxicillin trihydrate | 482.4 mg |
| | Sodium amoxicillin | 111.96 mg |
| | Methocel K100LV | 150 mg |
| B. | Amoxicillin trihydrate | 603 mg |
| | Methocel K100LV | 150 mg |
| C. | Amoxicillin trihydrate | 422.1 mg |
| | Sodium amoxicillin | 167.9 mg |
| | Methocel K100LV | 90.45 mg |
| | Methocel K4M | 60.3 mg |
| D. | Amoxicillin trihydrate | 500 mg |
| | Methocel K100LV | 62.5 mg |
| | Methocel K4M | 62.5 mg |

All tests were conducted as described above.

Results

A. Release of amoxicillin from a formulation containing 20% sodium amoxicillin based in Methocel K100LV (Formulation A) was 89.5% after 8 hrs, compared to 86.72% from a formulation containing amoxicillin trihydrate without sodium amoxicillin (Formulation B) after 8 hrs.

B. Release of amoxicillin from a formulation containing 70% amoxicillin trihydrate and 30% sodium amoxicillin, in which the polymer was a mixture of 40% Methocel K4M and 60% Methocel k100LV (Formulation C) was 71.07% after 8 hrs.

C. Release of amoxicillin from a formulation containing 80% amoxicillin trihydrate and 20% a 50:50 mixture of Methocel K4M and Methocel K100LV (Formulation D) was 46.48% after 6 hrs, compared to 31.36% from a formulation of the same drug:polymer ratio, where instead of the mixture of polymers the polymer was Methocel K4M and 79.34% from a similar formulation which contained Methocel K100LV instead of the mixture of polymers.

D. The rate of release can be increased by using Methocel K100LV. Addition of 20% sodium amoxicillin does not cause a substantial change in the rate of release compared to a formulation of similar constitution without sodium amoxicillin. The rate of release of amoxicillin from matrix tablets can be controlled by using mixtures of Methocel K100LV and Methocel K4M.

Example 2

Matrix Tablets Containing Eudragit and Alginate

Materials and Methods

Preparation of Matrix Tablets

Various mixtures of amoxicillin with Eudragit S100 and sodium alginate were prepared as in Example 1, geometrically mixed and manually compressed under tons for 30 sec. The surfaces of the tablet obtained were concave. The diameter of the tablets was 12 mm. The 12 mm diameter tablets contained 500 mg active agent (amoxicillin trihydrate), or 603 mg for some of the formulations.

The following formulation were prepared:

50% Eudragit S100

30%, sodium alginate

50% sodium alginate

The tablets were placed in the dissolution tester and DRT was performed as in Example 1. The dissolution test was carried out over 5 hrs.

Materials

In addition to the materials listed in Example 1, the following materials were used:

| | |
|---|---|
| Eudragit S100 | -Rhom Pharma |
| Sodium alginate | -Sigma, Israel |

Results

Release of amoxicillin from a formulation containing 50% Eudragit S100 was 75.2% after 5hrs.
Release of amoxicillin from a formulation containing 50% sodium alginate was 22.2% after 5 hrs.
Release of amoxicillin from a formulation containing 30% sodium alginate was 39% after 5hrs.
In contrast,
Release of amoxicillin from a formulation containing 50% Methocel K4M was 14.76% after 5 hrs. Release of amoxicillin from a formulation containing 50% Methocel K100LV was 28.83% after 5 hrs.
Release of amoxicillin from formulation containing 30% Methocel K4M was 18.2% after 5 hrs.
Release of amoxicillin from a formulation containing 30% Methocel K100LV was 46.56% after 5 hrs.

Summary

Release of amoxicillin from Eudragit S100 was the fastest, compared to other formulations which were tested, due to the solubility of the polymer at pH=6. Release of amoxicillin from sodium alginate was slower than from Eudragit S100 and Methocel K100LV, but faster than from Methocel K4M.

Example 3

Release of Amoxicillin from Methocel K100LV Tablets

Materials and Methods

A. Preparation of Tablets

Following the procedure of the previous Examples, the following tablets were prepared:

| | A3 | B3 | C3 |
|---|---|---|---|
| Amoxicillin 3H$_2$O (Compact) | 603.75 | 603.75 | 603.75 |
| Methocel K100LV | 120.75 | 120.75 | 131.85 |
| Avicel pH 101 | — | 55.50 | 55.50 |
| Magnesium Stearate | 10.0 | 10.0 | 10.0 |
| Aerosil 200 | 10.0 | 10.0 | 10.0 |
| Total wt (mg) | 744.50 | 800.00 | 811.10 |

B. Determination of Rate of Release of Amoxicillin from the Tablets

1. Instruments: The dissolution tester of Example 1 was used.
2. The matrix tablets were placed in standard baskets. Rate of dissolution was determined as in Example 1 (at 100rpm, 37° C., 900ml pH=7.4 buffer as extraction solution). Aliquots of 5 ml were removed from the extraction solution every 0.5, 1, 2, 3, 4, 5, 6, 7, and 8 hrs, and 5 ml buffer simultaneously added to maintain constant volume. The content of active agent was determined spectrophotometrically as describe in Example 1. Six tablets of each batch were tested. In tablets containing Avicel the extraction solution became turbid and therefore the aliquots were filtered.

Results

A. Release of Amoxicillin from Formulations based on Metitocel K100KLV (Formulations Nos. A3, B3 and C3)

| | A3 | | B3 | | C3 | |
|---|---|---|---|---|---|---|
| hrs | mg | % | mg | % | mg | % |
| 0.5 | 76.45 ± 11.72 | 12.66 ± 1.93 | 109.72 ± 22.11 | 18.17 ± 3.66 | 81.44 ± 8.43 | 13.48 ± 1.39 |
| 1 | 128.71 ± 16.59 | 21.31 ± 1.74 | 158.64 ± 28.76 | 26.27 ± 4.76 | 118.73 ± 10.82 | 19.64 ± 1.78 |
| 2 | 223.82 ± 19.44 | 37.07 ± 3.22 | 244.71 ± 33.39 | 40.53 ± 5.53 | 192.98 ± 12.37 | 31.96 ± 2.05 |
| 3 | 318.30 ± 20.13 | 52.72 ± 3.33 | 334.48 ± 30.71 | 55.40 ± 5.08 | 275.81 ± 21.35 | 45.68 ± 3.53 |
| 4 | 403.71 ± 19.79 | 66.86 ± 3.28 | 408.23 ± 34.91 | 67.61 ± 5.78 | 343.57 ± 13.67 | 56.90 ± 2.27 |
| 5 | 484.41 ± 23.04 | 80.23 ± 3.81 | 475.37 ± 29.90 | 78.73 ± 4.95 | 419.44 ± 12.74 | 69.47 ± 2.11 |
| 6 | 546.03 ± 26.26 | 90.44 ± 4.35 | 539.98 ± 42.79 | 89.43 ± 7.08 | 484.33 ± 16.85 | 80.22 ± 2.79 |
| 7 | 596.59 ± 20.95 | 98.81 ± 3.47 | 602.25 ± 37.29 | 99.75 ± 6.17 | 531.79 ± 18.67 | 88.08 ± 3.09 |
| 8 | 619.09 ± 13.19 | 102.54 ± 2.27 | 638.87 ± 29.86 | 105.81 ± 4.95 | 574.21 ± 17.99 | 95.10 ± 2.98 |

The formulations of this example were prepared for in vivo experiments.

Example 4

In vivo Experiment

Methods

Twelve healthy male volunteers, aged 24–30, participated in the in vivo evaluation of the A3 dosage form of Example 3. All volunteers gave informed consent to in participation and the study protocol was approved by a Helsinki Ethics Committee. The participants were randomized in a two-way crossover fashion.

Blood samples were collected periodically over 24 hrs and were assayed by HPLC.

Blood Amoxicillin Assay

A. Preparation of Fluorimetric Chromophor

Human plasma (0.5 ml), 1 ml standard solution of amoxicillin at various concentrations (for preparation of the calibration curve), 1.5 ml water and 1.5 ml 10% TCA solution (to precipitate proteins) were mixed and centrifuged for 5 min at 2000 rpm.

NaOH (2N, 0.25 ml) was added to a 5 ml aliquot removed from the top layer of the centrifugate. After 5 min the mixture was incubated in the dark for 20 min. at 50° C. with HCl (2N, 0.20 ml) and 0.002% Hg C12 solution in 0.5M phosphate buffer (1ml). The test tube were cooled to room temperature and saturated ethyl acetate/water solution was added. The mixture was vigorously vortexed for 5 min, in the dark, and centrifuged for 10 min. at 4000 rpm. 2 ml aliquots were removed from the organic phase and were vacuum dried. 100μl methanolic methyl anthranylate solution were added to the dry sample as internal standard.

B. Fluorimetric Determination

Determination was carried out by HPLC (Kontron Instruments, SFM25 fluorimetric detector):

Column:C=18, 150 mm long, mobile phase methanol:water (45:55);

Flowrate: 1ml/min;

Temperature: 55° C.;

Excitation wavelength:355;

Emission wavelength:435;

Fluorimetric detector voltage:700(±100) (High voltage);

Volume injected:20 μl;

Elution time:6 min.

Results

The mean concentration vs. time profile of active amoxicillin is shown in FIG. 1. It can be seen that both $C_{max}$ and AUC were significantly higher for the prior art capsules. The differences in the pharmacokinetic parameters which seem to indicate poor bioavailability have no relevance from the therapeutic point of view. The important factor is the time period over the MIC. High $C_{max}$ values do not correspond to increased efficacy.

As shown in FIG. 2, the sustained release formulation provides 1.5 hrs greater coverage than the capsules for MIC=0.5 mg/L and about 3 hrs longer for MIC=0.2 mg/L.

The pharmacodynamic profile of amoxicillin can be described by the sigmoidal $E_{max}$ model with a shape parameter larger than 1.5 (characterized by a steep profile) as described in FIG. 3, where the MIC is the $EC_{50}$ value. This presentation clearly explains the situation where the drug concentrations that are significantly greater than the MIC are close to the maximal effect $E_{max}$ and contribute only little to the efficacy.

What is claimed is:

1. A pharmaceutical controlled-release oral drug delivery system comprising as active ingredient at least one β-lactam antibiotic agent having a specific absorption site in the small intestine in combination with a polymeric matrix, optionally further containing additional pharmaceutically acceptable constituents, wherein at least 50% up to but not more than 67.61±5.78% of said β-lactam antibiotic agent is released from said matrix within 3 to 4 hours from oral administration and the remainder of the pharmaceutical agent is released at a controlled rate.

2. A drug delivery system according to claim 1 wherein said β-lactam antibiotic drug is selected from the group consisting of cephalosporins and penicillins, and pharmaceutically acceptable salts and derivatives thereof.

3. A drug delivery system according to claim 2 wherein said cephalosporin or derivative thereof is cefadroxil, cefalexin, cefaclor, cefprozil, cefuiroxime, cefoxitin, cefpodoxime, cefixime, cefuroxime axetil, or cefpodoxime proxetil.

4. A drug delivery system according to claim 2 wherein said penicillin is penicillin G, penicillin V, amoxicillin, ampicillin, nafcillin, oxacillin, cloxacillin or dicloxacillin, pharmaceutically acceptable salts thereof or pharmaceuticlly acceptable derivatives thereof.

5. A drug delivery system according to claim 4 wherein said β-lactam antibiotic agent is amoxicillin trihydrate.

6. A drug delivery system according to claim 2 comprising a β-lactamase inhibitor.

7. A drug delivery system according to claim 6 wherein said β-lactamase inhibitor is clavulonic acid, sulbactam or pharmaceutically acceptable salts thereof.

8. A drug delivery system according to claim 7 wherein said active ingredient is amoxicillin and said β-lactamase inhibitor is clavulonic acid.

9. A drug delivery system according to claim 1 wherein said polymeric matrix comprises a hydrophilic polymer.

10. A drug delivery system according to claim 9 wherein said polymer is selected from the group consisting of hydrophilic cellulose derivatives, hydrophilic polyacrylamide derivatives, proteins, alginates, arabinogalactane, chitosan and hydrophilic methacrylic acid derivatives.

11. A drug delivery system according to claim 10 wherein said hydrophilic cellulose derivative is selected from the group consisting of methyl cellulose, hydroxypropyl methylcellulose, hydroxyethyl cellulose, hydroxypropyl cellulose, carboxymethyl cellulose, sodium carboxymethyl cellulose and hydroxyethyl methyl cellulose.

12. A drug delivery system according to claim 10 wherein said proteins are egg albumin, bovine albumin, human albumin or soy bean protein, in native or denatured form.

13. A drug delivery system according to claim 1 wherein said polymeric matrix comprises a hydrophobic polymer.

14. A drug delivery system according to claim 13 wherein said polymer is selected from the group consisting of hydrophobic cellulose derivatives, fats, hydrophobic polyacrylamide and polyamide derivatives and hydrophobic methacrylic acid derivatives.

15. A drug delivery system according to claim 14 wherein said hydrophobic cellulose derivative is ethyl cellulose.

16. A drug delivery system according to claim 14 wherein said fat is glycerol palmitostearate, beeswax, glycowax, castorwax, carnaubawax, glycerol monostearate or stearyl alcohol.

17. A drug delivery system according to claim 1 wherein said polymeric matrix comprises a mixture of hydrophilic polymers, a mixture of hydrophobic polymers or a mixture of hydrophilic and hydrophobic polymers.

18. A drug delivery system according to claim 17 wherein said hydrophilic polymer is selected from hydrophilic cellulose derivatives, proteins, alginates, arabinogalactane, chitosan and hydrophilic methacrylic acid derivatives and said hydrophobic polymer is selected from hydrophobic cellulose derivatives, waxes and hydrophobic methacrylic acid derivatives.

19. A drug delivery system according to claim 1 further comprising a pharmaceutically acceptable additive selected from salts, polyethylene glycol and surfactants.

20. A drug delivery system according to claim 1 in dosage unit form.

21. A drug delivery system according to claim 20 which is in the form of a mono- or double-layer tablet, a disintegrating granulated tablet, or a capsule, which may be coated with a pharmaceutically acceptable coating.

* * * * *

UNITED STATES PATENT AND TRADEMARK OFFICE
CERTIFICATE OF CORRECTION

PATENT NO. : 6,399,086 B1
DATED : June 4, 2002
INVENTOR(S) : Ifat Katzhendler, Amnon Hoffman and Michael Friedman It is certified that error appears in the above-identified patent and that said Letters Patent is hereby corrected as shown below:

Column 1,
Line 9, "incorporatedin" should read -- incorporated in --;
Line 57, "o antimicrobial" should read -- antimicrobial --.

Column 3,
Line 26, "n=71.5" should read -- n=1.5 --.

Column 4,
Line 54, "fiber" should read -- further --.

Column 5,
Line 9, "tablet surfaces are" should read -- tablet's surface area --;
Line 35, "surface are" should read -- surface area --;
Line 43, "egg, albumin" should read -- egg albumin --.

Column 7,
Line 11, "by s the" should read -- by the --;
Line 50, "aceitc" should read -- hydrochloric acid --.

Column 8,
Line 34, "Concentration on" should read -- Concentration of --;
Line 35, "Agent of" should read -- Agent on --.

Column 9,
Line 1, "Size on" should read -- Size of --;
Line 1, "Granulate of" should read -- Granulate on --;
Line 29, "25" should read -- 0.25 --;
Line 57, "1.450 Flake NF" should read -- 1,450 Flake NF --;
Line 58, "4.600 Flake NF" should read -- 4,600 Flake NH --;

Column 10,
Line 47, "lo agent" should read -- agent --;
Line 53, "NaHCO03" should read -- NaHCO3 --.

Column 12,
Line 53, "under tons" should read -- under 5 tons --;
Line 57, "formulation" should read -- formulations --.

Column 13,
Lines 8 and 12, "Shrs." should read -- 5 hrs. --.

UNITED STATES PATENT AND TRADEMARK OFFICE
CERTIFICATE OF CORRECTION

PATENT NO. : 6,399,086 B1
DATED : June 4, 2002
INVENTOR(S) : Ifat Katzhendler, Amnon Hoffman and Michael Friedman It is certified that error appears in the above-identified patent and that said Letters Patent is hereby corrected as shown below:

Column 14,
Line 24, "Metitocel" should read -- Methocel --.

Column 15,
Line 58, "cefuiroxime" should read -- cefuroxime --.

Column 16,
Line 5, "claim 2 comprising" should read -- claim 2 further comprising --.

Signed and Sealed this

Twenty-eighth Day of February, 2006

JON W. DUDAS
*Director of the United States Patent and Trademark Office*